United States Patent
Maksyagin

(10) Patent No.: US 11,153,698 B2
(45) Date of Patent: Oct. 19, 2021

(54) SYSTEMS FOR AUTHORIZING PERFORMANCE OF AN OPERATION BY A HEARING DEVICE

(71) Applicant: SONOVA AG, Staefa (CH)

(72) Inventor: Alexander Maksyagin, Ebmatingen (CH)

(73) Assignee: Sonova AG, Staefa (CH)

( * ) Notice: Subject to any disclaimer, the term of this patent is extended or adjusted under 35 U.S.C. 154(b) by 0 days.

(21) Appl. No.: 16/547,452

(22) Filed: Aug. 21, 2019

(65) Prior Publication Data

US 2021/0058723 A1    Feb. 25, 2021

(51) Int. Cl.
*H04R 25/00* (2006.01)
*H04R 1/10* (2006.01)
*G16H 10/60* (2018.01)
*H04R 3/00* (2006.01)

(52) U.S. Cl.
CPC .......... *H04R 25/70* (2013.01); *H04R 1/1041* (2013.01); *H04R 25/558* (2013.01); *G16H 10/60* (2018.01); *H04L 2209/80* (2013.01); *H04L 2209/88* (2013.01); *H04R 3/005* (2013.01); *H04R 25/43* (2013.01)

(58) Field of Classification Search
CPC combination set(s) only.
See application file for complete search history.

(56) References Cited

U.S. PATENT DOCUMENTS

| | | | |
|---|---|---|---|
| 7,216,231 B2 | 5/2007 | Gehrmann | |
| 9,439,008 B2 | 9/2016 | Shennib | |
| 9,774,965 B2 | 9/2017 | Siddhartha et al. | |
| 10,785,585 B2* | 9/2020 | Pedersen | H04R 25/554 |
| 2006/0015463 A1* | 1/2006 | Gupta | G06Q 20/401 |
| | | | 705/52 |
| 2010/0205447 A1 | 8/2010 | Waldmann | |
| 2016/0173278 A1 | 6/2016 | Pedersen et al. | |

(Continued)

FOREIGN PATENT DOCUMENTS

| | | |
|---|---|---|
| EP | 3783922 | 2/2021 |
| WO | 2016078711 | 5/2016 |
| WO | 2018091079 | 5/2018 |

OTHER PUBLICATIONS

European Search Report received in International Application No. 20191664.0, dated Jan. 26, 2021.

*Primary Examiner* — Angelica M McKinney
(74) *Attorney, Agent, or Firm* — ALG Intellectual Property, LLC

(57) ABSTRACT

An exemplary authorization system is located remotely from a hearing device that is configured to facilitate hearing by a recipient. The authorization system comprises a memory storing instructions and a processor communicatively coupled to the memory. The processor is configured to execute the instructions to: receive, from a client in communication with the hearing device, a request for the hearing device to perform an operation; determine, based on device characteristic data that is representative of one or more characteristics specific to the hearing device, that the operation is valid for the hearing device; and transmit, in response to determining that the operation is valid for the hearing device, an authorization message to the hearing device, the authorization message authorizing the hearing device to perform the operation requested by the client.

20 Claims, 8 Drawing Sheets

(56) References Cited

U.S. PATENT DOCUMENTS

2016/0173997 A1* 6/2016 Pedersen ................ H04R 25/00
  381/314
2016/0212552 A1   7/2016 Schneider et al.
2016/0352524 A1* 12/2016 Kinney ................ H04L 63/083
2019/0335281 A1* 10/2019 Dickmann ........... H04R 25/556

* cited by examiner

SYSTEMS FOR AUTHORIZING PERFORMANCE OF AN OPERATION BY A HEARING DEVICE

BACKGROUND INFORMATION

Hearing devices (e.g., hearing aids) are used to improve the hearing capability and/or communication capability of recipients. Such hearing devices are configured to process a received input sound signal (e.g., ambient sound) and then provide the processed input sound signal to the recipient (e.g., by way of a microphone or receiver placed in the recipient's ear canal). Such hearing devices operate according to hearing device settings, which may be adjusted according to the individual preferences and needs of a recipient based on the recipient's specific hearing capability/deficiency (e.g., hearing loss). The process of adjusting hearing device settings (e.g., hearing programs, signal processing parameters, threshold levels, etc.) is typically referred to as a fitting operation and is conventionally performed by a fitting client ("client"), which may be implemented by any suitable combination of hardware and/or software communicatively connected to a hearing device.

Any one of a plurality of different clients may communicatively connect to a hearing device and attempt to adjust hearing device settings for the hearing device. However, certain clients may not be configured to correctly fit the hearing device to the recipient. For example, a client may have design or implementation flaws, may be a non-medical class client, and/or may be controlled by an entity that specifically seeks to do harm to the recipient. Clients such as these or others may attempt to instruct the hearing device to modify its hearing device settings incorrectly, which may cause the hearing device to operate in a suboptimal or unsafe manner. For example, a malfunctioning and/or malicious client may instruct a hearing device to increase the maximum power output (MPO) threshold of the hearing device, which may cause permanent damage to the recipient's hearing capability.

BRIEF DESCRIPTION OF THE DRAWINGS

The accompanying drawings illustrate various embodiments and are a part of the specification. The illustrated embodiments are merely examples and do not limit the scope of the disclosure. Throughout the drawings, identical or similar reference numbers designate identical or similar elements.

DETAILED DESCRIPTION

Figure 1:
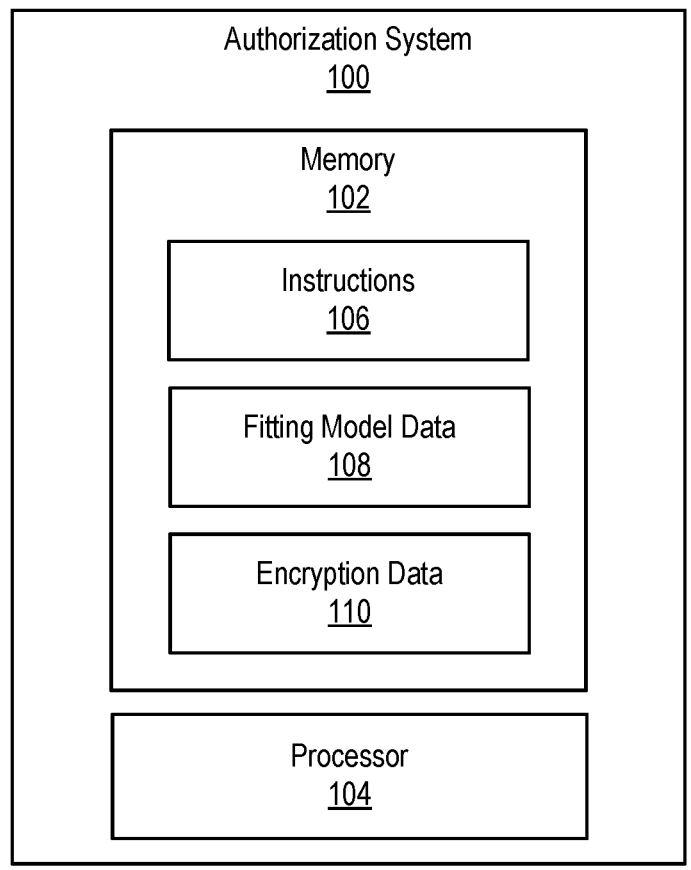
FIG. 1 illustrates an exemplary authorization system according to principles described herein.

Systems for authorizing performance of an operation by a hearing device are described herein. As will be described in more detail below, an exemplary system includes a hearing device configured to facilitate hearing by a recipient and store device characteristic data representative of device characteristics specific to the hearing device, a client in communication with the hearing device, and an authorization system located remotely from the hearing device and the client. The authorization system is configured to receive, from the client, a request for the hearing device to perform an operation, determine, based on the device characteristic data, that the operation is valid for the hearing device, and transmit, in response to determining that the operation is valid for the hearing device, an authorization message to the hearing device. The authorization message transmitted by the authorization system authorizes the hearing device to perform the operation requested by the client.

To illustrate an example, a client (e.g., a hearing device fitting mobile application, a cloud-based hearing device fitting service, a computing device configured to execute fitting software, etc.) may communicatively connect to a hearing device (e.g., a hearing aid device) and request that the hearing device perform an operation. For example, the client may request that the hearing device change a safety threshold level stored in a memory of the hearing device. In accordance with the systems and methods described herein, prior to the hearing device performing the operation, the request is transmitted to an authorization system remote from the client (e.g., connected to the client by way of a network) configured to determine whether the requested operation is valid for the hearing device (e.g., whether the operation would result in the hearing device operating properly and/or safely). If the authorization system determines that the operation is valid, the authorization system may transmit an authorization message to the hearing device that authorizes the hearing device to perform the operation requested by the client. If the authorization system determines that the requested operation is not valid (e.g., the operation would result in the hearing device operating improperly and/or unsafely), the authorization system may prevent the hearing device from performing the operation.

By utilizing an authorization system to authorize operations performed by hearing devices, it is possible to ensure that the hearing devices operate properly and safely regardless of which client or type of client requests a particular operation to be performed. In addition, with systems such as those described herein, safety-checking of requested operations is performed by the authorization system as opposed to the hearing device or the client. As such, it is possible to outsource potentially resource consuming computations to the authorization system. Moreover, systems such as those described herein may allow a client to change, for example, a setting of a hearing device anonymously (e.g., without disclosing the identities of the client, the recipient, or the hearing device). In so doing, it is possible to maintain privacy expectations of recipients of hearing devices and/or other entities associated with fitting hearing devices recipients. In addition, a client operating in accordance with the systems and methods described herein does not need to be certified as a medical device, which results in cost savings. Further, with systems and methods such as those described herein, it is not necessary to update clients with software patches to safety-checking mechanisms. Other benefits of the hearing devices and systems described herein will be made apparent herein.

FIG. 1 illustrates an exemplary authorization system 100 ("system 100"). As shown, system 100 may include, without limitation, a memory 102 and a processor 104 selectively and communicatively coupled to one another. memory 102 and processor 104 may each include or be implemented by hardware and/or software components (e.g., processors, memories, communication interfaces, instructions stored in memory for execution by the processors, etc.). In some examples, memory 102 and processor 104 may be distributed between multiple devices and/or multiple locations as may serve a particular implementation.

Memory 102 may maintain (e.g., store) executable data used by processor 104 to perform any of the operations associated with system 100 described herein. For example, memory 102 may store instructions 106 that may be executed by processor 104 to perform any of the operations associated with system 100 described herein. Instructions 106 may be implemented by any suitable application, software, code, and/or other executable data instance.

Memory 102 may also maintain any data received, generated, managed, used, and/or transmitted by processor 104. For example, as shown, memory 102 may maintain fitting model data 108 and encryption data 110.

Fitting model data 108 may include data representative of one or more fitting models used to model fitting of a hearing device to a recipient. As will be described herein, fitting model data 108 may be used in certain examples to determine whether a requested operation would result in a hearing device working properly.

Encryption data 110 may include any data that may be used to facilitate secure communications between authorization system 100 and a hearing device. For example, encryption data 110 may include data representative of a private key used in asymmetric cryptography to sign messages provided to a hearing device and/or a client. It is understood that such a private key may be write-protected and read-protected in memory 102 so that the private key is kept secret.

Memory 102 may maintain additional or alternative data in other implementations.

Processor 104 may be configured to perform (e.g., execute instructions 106 stored in memory 102 to perform) various processing operations associated with authorizing an operation to be performed by a hearing device. For example, processor 104 may receive, from a client in communication with the hearing device, a request for the hearing device to perform an operation, receive, from the hearing device, device characteristic data that is representative of one or more characteristics specific to the hearing device, determine, based on the device characteristic data, that the operation is valid for the hearing device, and transmit, in response to determining that the operation is valid for the hearing device, an authorization message to the hearing device, the authorization message authorizing the hearing device to perform the operation requested by the client. These and other operations that may be performed by processor 104 are described herein.

System 100 may be located remotely (e.g., at a remotely-located server facility, in the cloud, etc.) from a hearing device and is configured to act as a gateway through which operation requests go through before the hearing device is permitted to perform an operation. In certain examples, system 100 may be implemented by, controlled by, or otherwise associated with a manufacturer of a hearing device and/or any other suitable entity. In so doing, the manufacturer of the hearing device and/or other entity may act through system 100 as an administrator that is able to manage operations (e.g., changes in hearing device settings) performed by hearing devices to ensure that the operations are performed only in a controlled manner, under supervision of the manufacturer. To that end, system 100 (e.g., processor 104) is configured to receive, from a client in communication with a hearing device, a request for the hearing device to perform an operation.

As used herein, a "client" may be implemented by any suitable combination of hardware and/or software that may be configured to communicate with a hearing device and request that the hearing device perform an operation (e.g., a read/write operation in memory of the hearing device). For example, a client may be implemented by a fitting application operating on a mobile device (e.g., a smartphone, laptop computer, tablet, etc.), a fitting system operated by fitting specialist located at a fitting facility (e.g., a hospital), a cloud-based fitting service, etc. It is understood that, with systems such as those described herein, it is not necessary for a client to be registered with system 100. As such, the client may remain anonymous while requesting performance of an operation by a hearing device. That is, according to systems such as those described herein, any anonymous client may submit an operation to be authorized by system 100.

As used herein, a "hearing device" may be implemented by any device configured to provide or enhance hearing to a recipient. For example, a hearing device may be implemented by a hearing aid configured to amplify audio content to a recipient, a sound processor included in a cochlear implant system configured to apply electrical stimulation representative of audio content to a recipient, a sound processor included in a stimulation system configured to apply electrical and acoustic stimulation to a recipient, or any other suitable hearing prosthesis. In some examples, a hearing device may be implemented by a behind-the-ear (BTE) hearing device configured to be worn behind an ear and/or at least partially within an ear canal of a recipient. With the systems described herein, it is also not necessary for the hearing device and/or its recipient to be registered/authenticated to system 100. As such, it is possible for the hearing device and/or the recipient to remain anonymous during the process of system 100 authorizing an operation. However, in certain alternative examples described herein, a hearing device and/or recipient may not be anonymous (e.g., the hearing device may be pre-registered and/or authenticated with system 100).

As used herein, an "operation" refers to any action or combination of actions that a client may request a hearing device to perform. For example, an operation requested by a client may request that a hearing device update hearing device firmware (e.g., to fix a bug in the firmware of the hearing device in the field), unlock an otherwise locked feature of the hearing device, and/or modify a setting, an operating parameter, a hearing program, etc. stored in a memory of the hearing device. In certain examples, an operation requested by a client may include a plurality of sub-operations that a hearing device is requested to perform.

In certain examples, all of the operation requests that are provided to the hearing device may be routed through system 100 for authorization. For example, each time a client requests adjustment of a setting, a hearing program, etc. associated with a hearing device, the request has to go through system 100 to determine whether the requested adjustment is valid for the hearing device.

In certain alternative examples, system 100 may be configured to authorize only a subset of the operations that may be performed by a hearing device. For example, a hearing device may operate in accordance with a first data set that controls general settings (e.g., volume) of the hearing device and a second data set that controls critical settings (e.g., the MPO threshold level) of the hearing device. In such examples, only operations associated with the second data set may have to be authorized by system 100. In another example, a hearing device may be configured with rules that dictate which operations require authorization and which operations do not. For operations that require authorization, the hearing device may notify a client in any suitable manner that a given operation requires authorization by system 100 prior to being performed.

To facilitate system 100 authorizing a requested operation, system 100 may utilize device characteristic data that is representative of one or more characteristics specific to a hearing device. In certain examples, the device characteristic data may be received directly or indirectly in any suitable way from the hearing device. The device characteristic data may include any data associated with the hearing device. For example, device characteristic data may include, but is not limited to, information regarding hearing loss characteristics of a recipient, information identifying the type of hearing device(s) used by the recipient, current hearing device settings, safety thresholds of the hearing device, current operating parameters of the hearing device, hearing programs used by the hearing device, etc.

System 100 may receive the device characteristic data in any suitable manner and at any suitable time. In certain examples, system 100 may receive the device characteristic data from the hearing device by way of the client. In certain alternative examples, system 100 may receive the device characteristic data directly from the hearing device without going through the client.

In certain examples, system 100 may receive the device characteristic data from the hearing device in response to a request provided by system 100 for the device characteristic data. For example, after system 100 receives a request for a hearing device to perform an operation from a client, system 100 may send a message to the hearing device (either through the client or directly to the hearing device) requesting that the hearing device provide the device characteristic data to system 100.

After system 100 receives the device characteristic data, system 100 is configured to use the device characteristic data to determine whether the requested operation is valid for the hearing device (e.g., whether the operation results in the hearing device functioning in an acceptable manner). System 100 may use the device characteristic data in any suitable manner. For example, system 100 may input the device characteristic data into one or more fitting models stored as fitting model data 108 in memory 102. If an output of a fitting model indicates that a requested operation would result in the hearing device operating properly (e.g., in a safe and acceptable manner), system 100 may determine that the operation is valid (also referred to herein as being acceptable) for the hearing device. Alternatively, if the output of the fitting model indicates that the requested operation would result in the hearing device operating improperly (e.g., an unsafe or unacceptable manner), system 100 may determine that the operation is not valid for the hearing device.

In certain alternative implementations, system 100 may not use a fitting model to determine whether a requested operation is valid. For example, the requested operation may not be associated with a fitting setting. As such, system 100 may determine whether the requested operation is valid without having to input the device characteristic data into a fitting model.

If system 100 determines that an operation is valid for a hearing device, system 100 is configured to transmit an authorization message to the hearing device that authorizes the hearing device to perform the operation requested by the client. Such an authorization message may be provided in any suitable manner as may serve a particular implementation.

In certain implementations, system 100 may use cryptography to generate and securely transmit an authorization message to a hearing device. For example, system 100 may use asymmetric cryptography to generate and transmit an authorization message. In such examples, system 100 may use a private key stored as part of encryption data 110 in memory 102 to generate a signed authorization message. Such a signed authorization message may have a signature that is produced by using the private key. The signed authorization message can then be verified in any suitable manner with a corresponding public key of system 100 that is stored by the hearing device. The signature included in a signed authorization message may include any suitable information. For example, the signature included in the signed authorization message may include a hash that is calculated based on the requested operation, the device characteristic data, and a nonce generated by the hearing device and that is encrypted based on the private key.

In certain alternative implementations, system 100 may use symmetric cryptography to authenticate and transmit an authorization message to a hearing device. In such examples, each hearing device may be associated with a unique key that is stored in respective memories of the hearing devices and by system 100 (e.g., in memory 102). Such unique keys may be used by system 100 in any suitable manner (e.g., for generation of message authentication codes) to authenticate and provide a signed authorization message to a hearing device. In certain examples, a nonce may also be used in combination with the symmetric cryptography to ensure that old communications cannot be reused in replay attacks.

Exemplary cryptographic schemes such as those described herein include using a nonce to, for example, prevent replay attacks. However, it is understood that, in certain alternative examples, a nonce may not be used together with the cryptography (e.g., asymmetric or symmetric cryptography) that is used to generate and securely transmit an authorization message to a hearing device.

If system 100 determines that an operation is not valid for a hearing device, system 100 may prevent the hearing device from performing the operation. This may be accomplished in any suitable manner. For example, system 100 may simply abstain from transmitting an authorization message to the hearing device. Alternatively, system 100 may transmit a message to the hearing device that specifically instructs the hearing device to not perform the operation.

Figure 2:
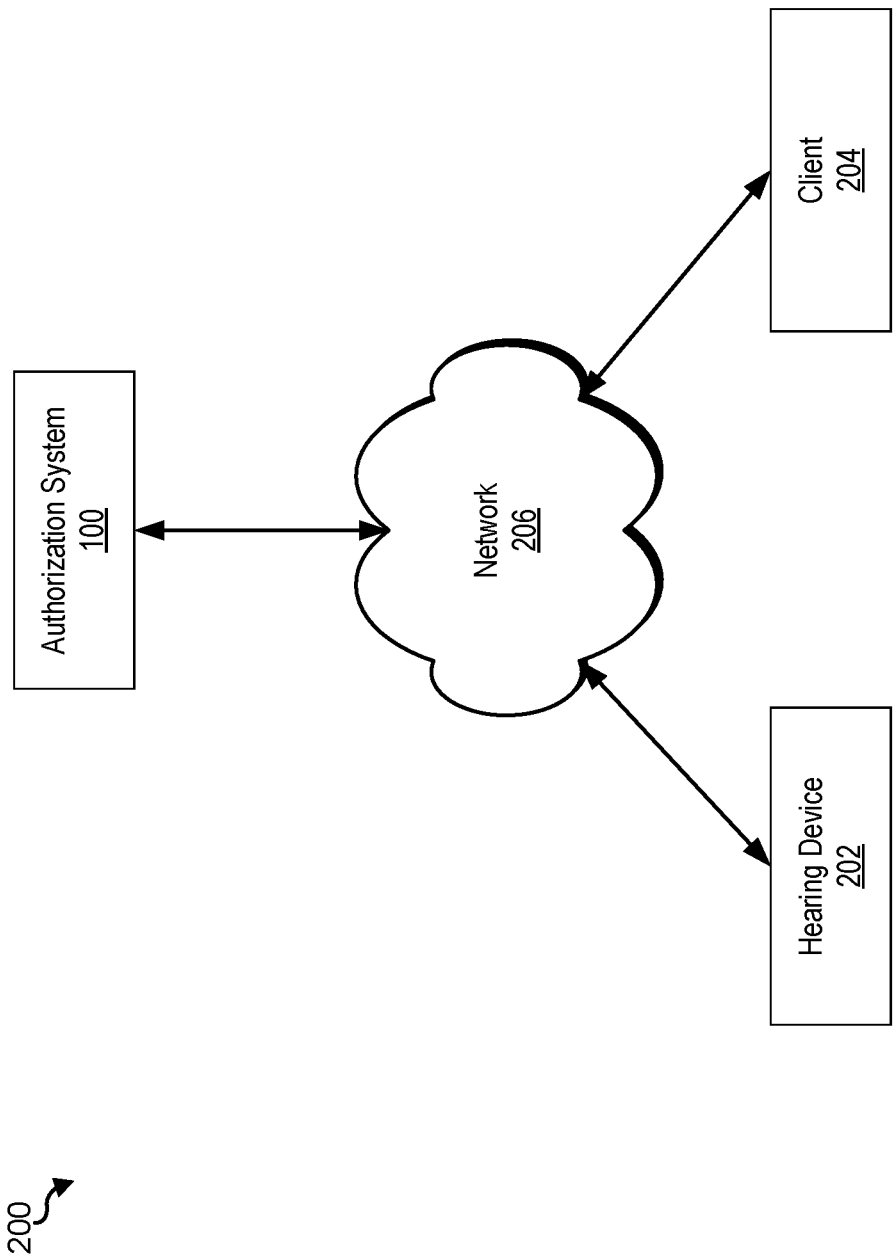
FIGS. 2 and 3 illustrate exemplary network configurations in which the authorization system shown in FIG. 1 may be implemented according to principles described herein.

System 100 may communicate with a hearing device and a client in any suitable manner to facilitate system 100 authorizing operations performed by the hearing device. For example, FIG. 2 shows an exemplary network configuration 200 in which system 100 is communicatively connected to a hearing device 202 and a client 204 by way of a network 206.

Hearing device 202 may be implemented by any type of hearing device configured to provide or enhance hearing to a recipient, such as those described herein. Although only one hearing device 202 is shown in FIG. 2, it is understood that hearing device 202 may be included in a system that includes more than one hearing device configured to provide or enhance hearing to a recipient. For example, hearing device 202 may be included in a binaural hearing system that includes two hearing devices, one for each ear. In such examples, hearing device 202 may be provided behind, for example, the left ear of the recipient and an additional hearing device may be provided behind the right ear of the recipient. When hearing device 202 is included as part of a binaural hearing system, hearing device 202 may communicate with the additional hearing device by way of a binaural communication link that interconnects hearing device 202 with the additional hearing device. Such a binaural communication link may include any suitable wireless or wired communication link as may serve a particular implementation.

Client 204 is configured to communicate with system 100 and hearing device 202 by way of network 206 and provide a request to system 100 and/or hearing device 202 for hearing device 202 to perform an operation. Although only one client 204 is shown in FIG. 2, it is understood that a plurality of different types of clients may be configured to communicate with hearing device 202 and potentially request that hearing device 202 perform an operation.

Network 206 may include any provider-specific wired or wireless network (e.g., a cable or satellite carrier network or a mobile telephone network), the Internet, a wide area network, or any other suitable network. Data may flow between system 100, hearing device 202, and client 204 using any communication technologies, devices, media, and protocols as may serve a particular implementation. For example, system 100, hearing device 202, and client 204 may communicate using any suitable communication technologies, devices, media, and/or protocols supportive of data communications, including, but not limited to, socket connections, Ethernet, data bus technologies, data transmission media, communication devices, media streaming technologies (e.g., video streaming technologies), Moving Picture Experts Group ("MPEG") protocols, Transmission Control Protocol ("TCP"), Internet Protocol ("IP"), File Transfer Protocol ("FTP"), Telnet, Hypertext Transfer Protocol ("HTTP"), HTTPS, Session Initiation Protocol ("SIP"), Simple Object Access Protocol ("SOAP"), Extensible Markup Language ("XML") and variations thereof, Real-Time Transport Protocol ("RTP"), User Datagram Protocol ("UDP"), Global System for Mobile Communications ("GSM") technologies, Code Division Multiple Access ("CDMA") technologies, Evolution Data Optimized Protocol ("EVDO"), 4G Long Term Evolution ("LTE"), WiMax, Time Division Multiple Access ("TDMA") technologies, radio frequency ("RF") signaling technologies, wireless communication technologies (e.g., BLUETOOTH, Wi-Fi, etc.), in-band and out-of-band signaling technologies, and other suitable communications technologies. While only one network 206 is shown to interconnect system 100, hearing device 202, and client 204 in FIG. 2, it will be recognized that these devices and systems may intercommunicate by way of multiple and/or different interconnected networks as may serve a particular implementation.

Figure 3:
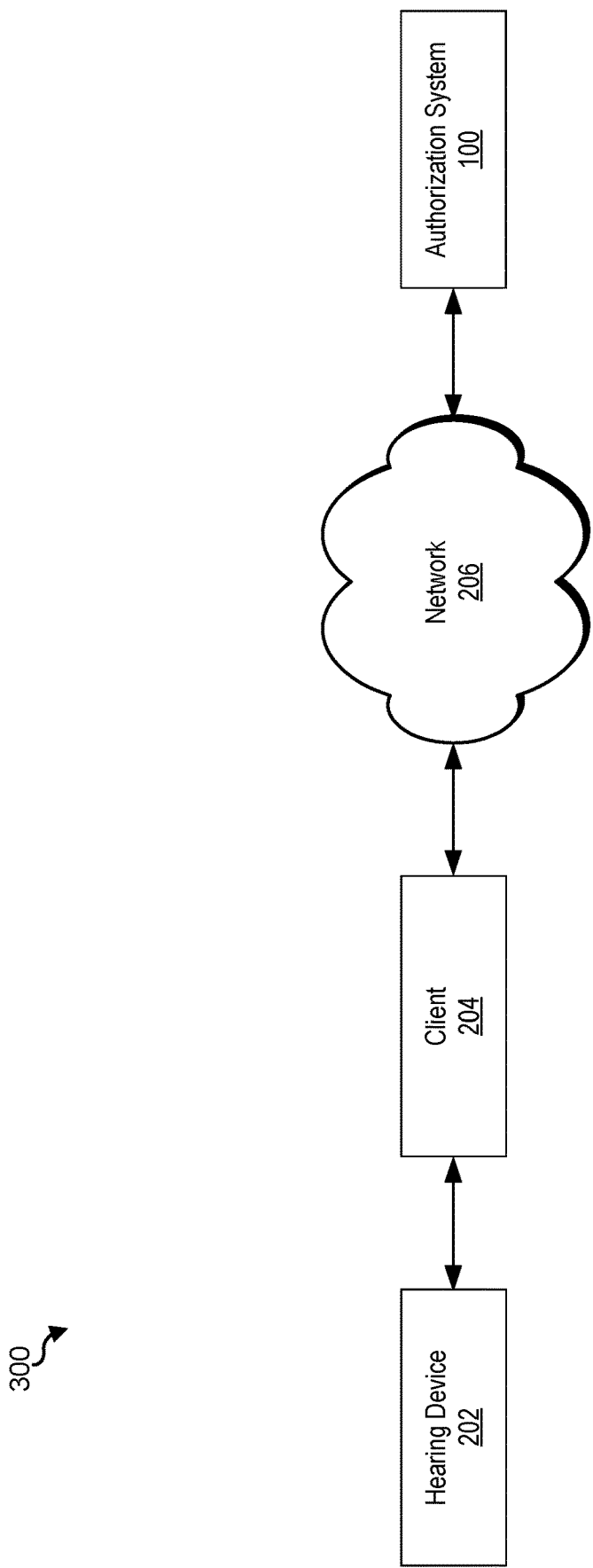

In certain examples, hearing device 202 may be configured to communicate with authorization system 100 by way of client 204. To illustrate, FIG. 3 shows another exemplary network configuration 300 in which hearing device 202 communicates directly with client 204, which in turn communicates with authorization system 100 by way of network 206. Hearing device 202 may communicate directly with client 204 by way of any suitable wired or wireless communication technology, such as those described herein.

In certain alternative implementations, system 100 may be configured to communicate indirectly and/or directly with hearing device 202. For example, system 100 may be configured to communicate with hearing device 202 by way of client 204 for some operations such as those described herein and may be configured to communicate directly with hearing device 202 (e.g., by way of network 206) for other operations.

Figure 4:
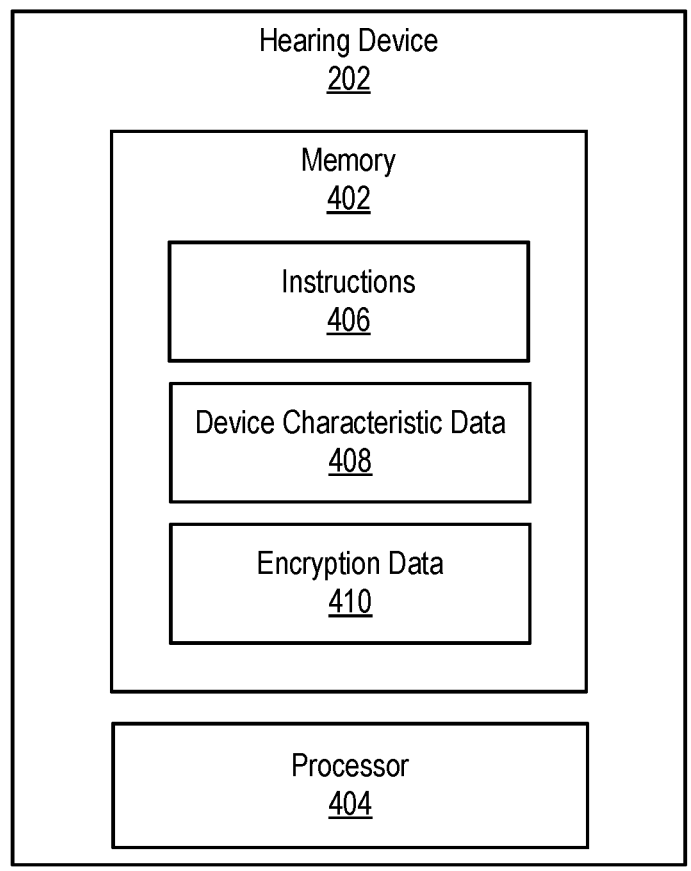
FIG. 4 illustrates an exemplary hearing device according to principles described herein.

FIG. 4 illustrates various components that may be included as part of hearing device 202 according to principles described herein. As shown in FIG. 4, hearing device 202 may include, without limitation, a memory 402 and a processor 404 selectively and communicatively coupled to one another. Memory 402 and processor 404 may each include or be implemented by hardware and/or software components (e.g., processors, memories, communication interfaces, instructions stored in memory for execution by the processors, etc.). In some examples, memory 402 and processor 404 may be distributed between multiple hearing devices (e.g., multiple hearing devices in a binaural hearing system) as may serve a particular implementation.

Memory 402 may be implemented by any suitable type of storage medium and may maintain (e.g., store) data utilized by processor 404. For example, memory 402 may store data representative of an operation program that specifies how processor 404 processes and delivers audio content to a recipient. To illustrate, memory 402 may maintain data representative of a first program that causes processor 404 to operate in a wireless audio rendering mode and a second program that causes processor 404 to operate in a normal mode in which processor 404 amplifies ambient sound detected by a microphone that is a part of hearing device 202. Memory 402 may maintain data representative of similar programs.

Memory 402 may maintain (e.g., store) executable data used by processor 104 to perform any of the operations associated with hearing device 202 described herein. For example, memory 402 may store instructions 406 that may be executed by processor 404 to perform any of the operations associated with hearing device 202 described herein. Instructions 406 may be implemented by any suitable application, software, code, and/or other executable data instance.

Memory 402 may also maintain any data received, generated, managed, used, and/or transmitted by processor 404. For example, as shown, memory 402 may maintain device characteristic data 408 and encryption data 410.

Device characteristic data 408 may include any data associated with a recipient and characteristics specific to the hearing device. For example, device characteristic data 408 may include information regarding hearing programs stored in memory 402, settings associated with hearing device 202, the type of hearing device, hearing loss characteristics of the recipient, and/or any other suitable data. At least some of device characteristic data 408 may be write-protected in memory 402. Such write-protected device characteristic data may include a setting of hearing device 202 that is not modifiable by hearing device 202 or client 204 unless authorized by system 100. For example, device characteristic data 408 may include an MPO threshold level setting that is write-protected and that is not modifiable by hearing device 202 or client 204 unless specifically authorized by system 100.

Encryption data 410 may include any suitable data that may facilitate hearing device 202 validating (e.g., authenticating) and/or decrypting messages transmitted from system 100 and/or client 204. For example, in certain implementations, encryption data 410 may include a public key that is paired with a corresponding private key stored in memory 102 of system 100. In certain examples, the public key stored in memory 402 may be write-protected. In addition, encryption data 410 may include any suitable data usable by hearing device 202 to generate a nonce that may be used to facilitate hearing device 202 securely receiving and/or validating messages received from system 100.

Processor 404 is configured to perform any suitable processing operation that may be associated with hearing device 202. For example, when hearing device 202 corresponds to a hearing aid device, such processing operations may include monitoring ambient sound, connecting to an external device (e.g., a smartphone, a television, etc.), and/or representing sound to a recipient via an in-ear microphone. In examples where hearing device 202 is included as part of a cochlear implant system, such processing operations may include directing a cochlear implant to generate and apply electrical stimulation representative of one or more audio signals (e.g., one or more audio signals detected by a microphone, input by way of an auxiliary audio input port, etc.) to one or more stimulation sites associated with an auditory pathway (e.g., the auditory nerve) of a recipient. Processor 404 may be implemented by any suitable combination of hardware and software.

In addition, hearing device 202 (e.g., processor 404) is configured to perform any suitable processing operation associated with hearing device 202 performing an operation requested by a client. For example, hearing device 202 is configured to provide device characteristic data to authorization system 100 to be used by system 100 to authorize an operation. Hearing device 202 may provide the device characteristic data to system 100 at any suitable time and in response to any suitable request. For example, hearing device 202 may transmit the device characteristic data based on a request provided by client 204 for hearing device 202 to perform an operation. In certain examples, client 204 may first send the request to hearing device 202. In such examples, hearing device 202 may inform client 204, in any suitable manner, that hearing device 202 cannot perform the requested operation unless authorized by system 100. Hearing device 202 may then identify system 100 and transmit the device characteristic data to system 100 (e.g., through client 204 or directly to system 100 without going through client 204). In certain alternative examples, hearing device 202 may receive a request from system 100 that requests transmission of the device characteristic data.

In certain examples, hearing device 202 may not actively transmit the device characteristic data to system 100. Rather, client device 204 may have access to memory 402 of hearing device 202 and may read out device characteristic data from memory 402 and forward the device characteristic data to system 100.

Based on the device characteristic data, hearing device 202 may receive, from system 100 by way of network 206, an authorization message. The authorization message authorizes hearing device 202 to perform the operation requested by client 204. Hearing device 202 may receive the authorization message in any suitable manner. For example, hearing device may receive the authorization message from system 100 by way of client 204. Alternatively, hearing device 202 may receive the authorization message directly from system 100 (e.g., without the authorization message going through client 204).

In certain examples, the authorization message received by hearing device 202 may be signed by system 100 using asymmetric cryptography. In such examples, in order to prevent attacks that replay old authorization messages, hearing device 202 may be configured to generate and provide a nonce to system 100. The nonce may correspond to an arbitrary number that is used just once in a cryptographic communication (e.g., for only one authorization message). The nonce may be used in any suitable manner by system 100 to encrypt and/or prepare the authorization message to be validated by hearing device 202.

In certain examples, the authorization message may be a signed authorization message that includes a signature that is generated based on a private key stored in memory 102 and that includes the nonce. In such examples, hearing device 202 may be configured to verify that the authorization message is from system 100. This may be accomplished in any suitable manner. For example, hearing device 202 may use a public key stored as part of encryption data 410 and the nonce to verify that the signed authorization message is valid (e.g., to verify the signature of the authorization message). If the signature verification is successful (e.g., if the generated nonce matches the nonce provided by system 100 in the signed authorization message), hearing device 202 may determine that the authorization message is verified (e.g., the requested operation is authorized and therefore can be performed). Alternatively, if the signature verification fails (e.g., if the generated nonce does not match the nonce provided by system 100), hearing device 202 may determine that the authorization message is not verified (e.g., the requested operation is not authorized and therefore is rejected or ignored).

In certain examples, hearing device 202 may be configured to transmit a confirmation message by way of network 206 to client 204 indicating that the operation has been performed. Additionally or alternatively, hearing device 202 may be configured to transmit the confirmation message to system 100 by way of network 206.

Figure 5:
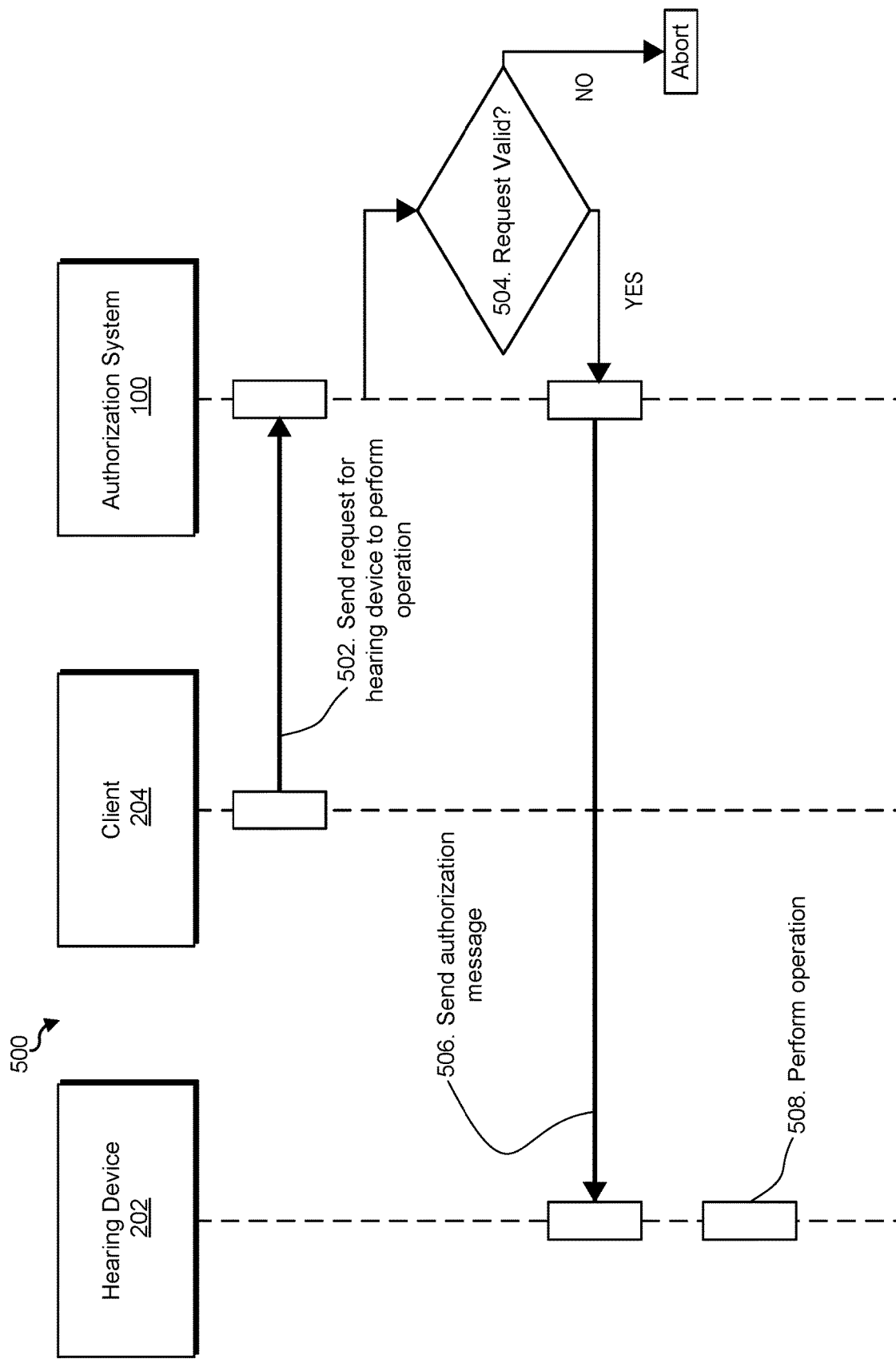
FIGS. 5-7 illustrate exemplary sequence diagrams depicting communications between and/or operations that may be performed by hearing devices, clients, and/or exemplary systems such as those described herein according to principles described herein.
Figure 6:
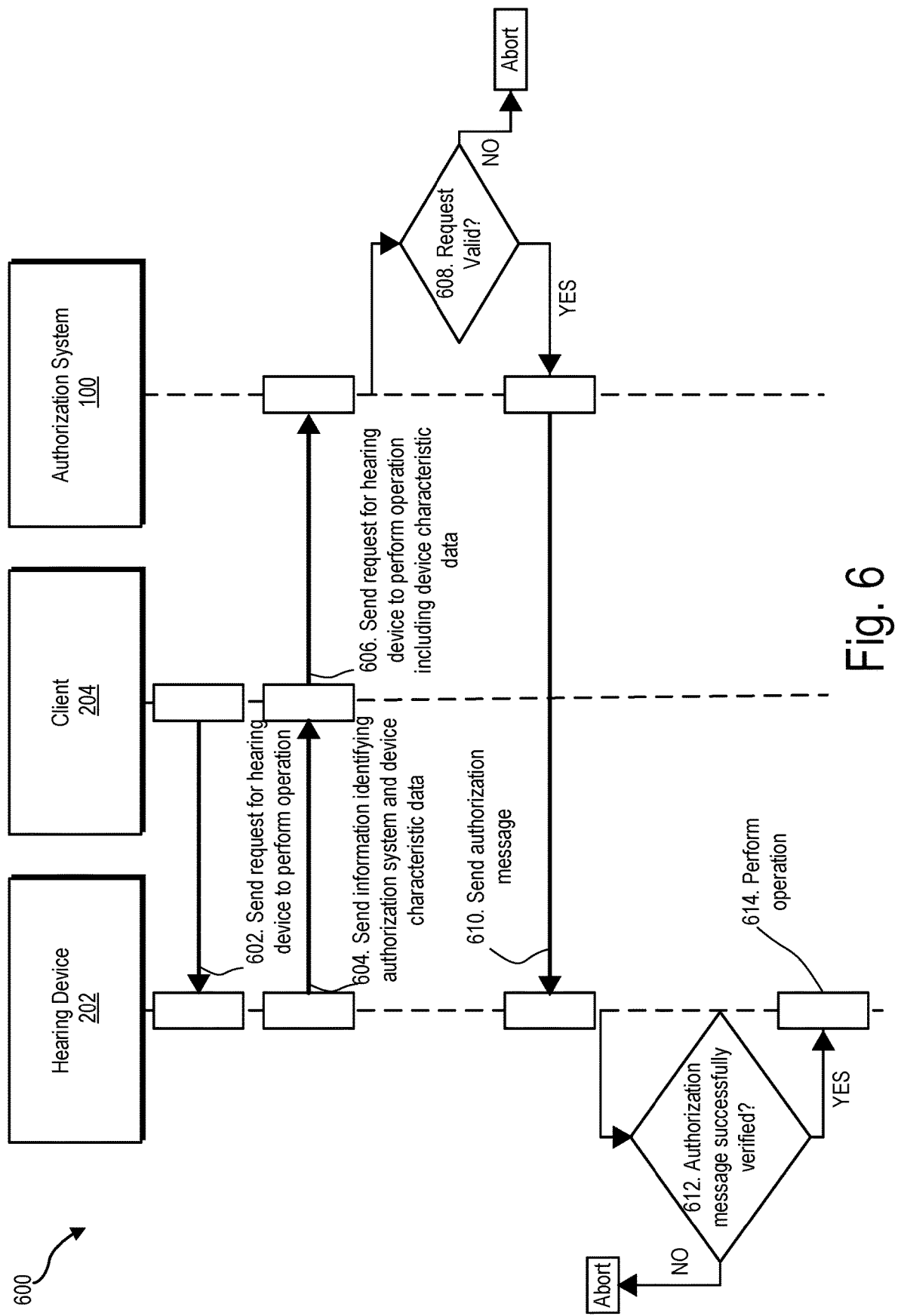
Figure 7:
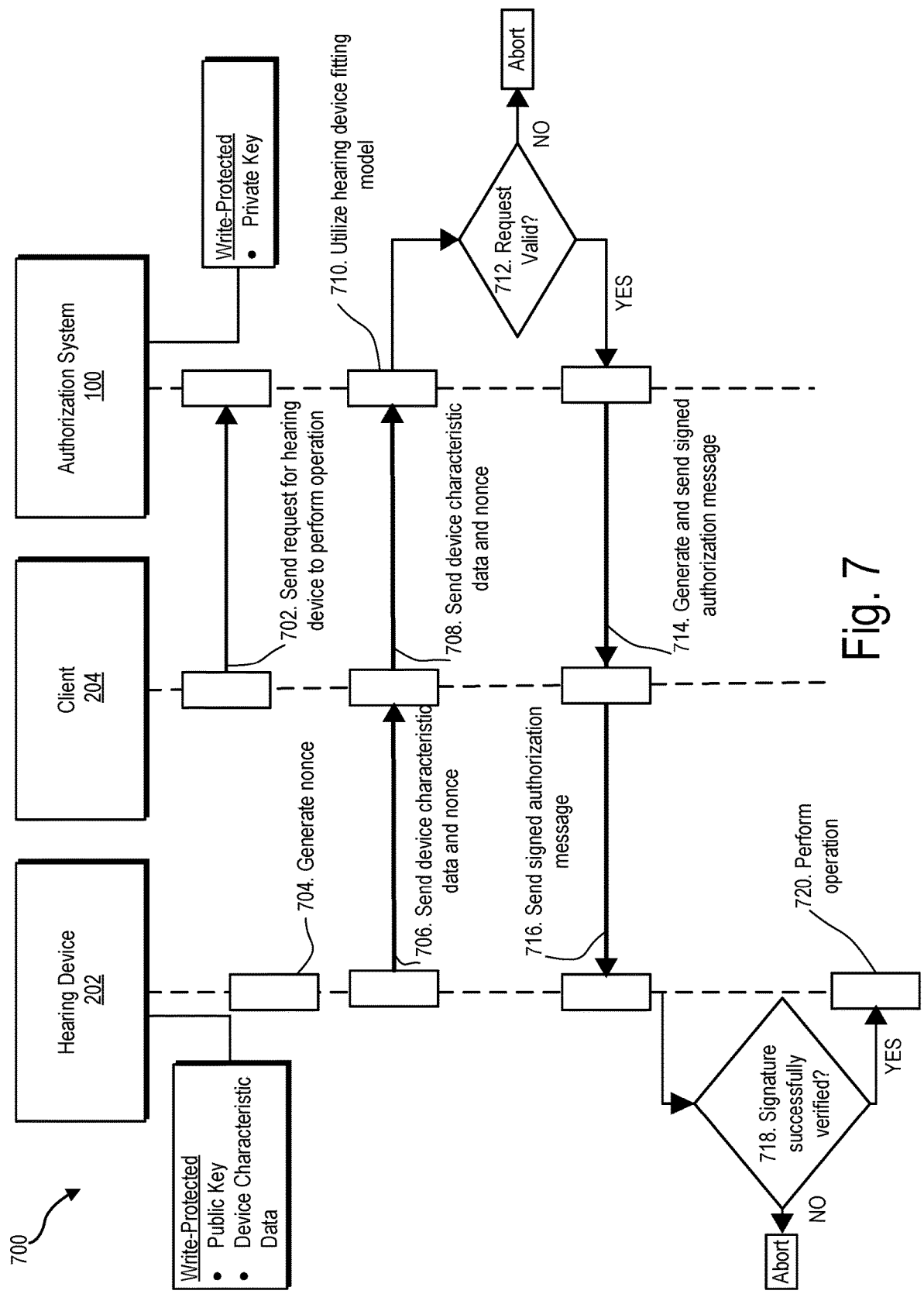

FIGS. 5-7 illustrate exemplary sequence diagrams 500, 600, and 700 depicting communications between and/or operations that may be performed by hearing device 202, client 204, and system 100.

As shown in FIG. 5, client 204 may send a request to system 100 for hearing device 202 to perform an operation in operation 502. In response to the request sent from client 204, system 100 may determine whether the request is valid in operation 504. For example, system 100 may determine that the requested operation would result in hearing device 202 operating in an unsafe or improper manner. In such a situation, system 100 may abort the process such that hearing device 202 does not perform the operation. Alternatively, system 100 may determine that the request would result in hearing device 202 operating in a safe and acceptable manner. In response to such a determination, system 100 may transmit an authorization message to hearing device 202 in operation 506. In response to the authorization message, hearing device 202 may perform the operation in operation 508.

In the example shown in FIG. 5, the authorization message is shown as being transmitted from system 100 to hearing device 202. However, it is understood that in certain implementations the authorization message may be transmitted to hearing device 202 by way of client 204.

In the exemplary sequence diagram 600 shown in FIG. 6, client 204 sends a request to hearing device 202 for hearing device 202 to perform an operation in operation 602. In response to the request, hearing device 202 may send information identifying system 100 and device characteristic data to client 204 in operation 604. Based on the information identifying system 100 and the device characteristic data, client 204 may send the device characteristic data and request for hearing device 202 to perform the operation to system 100 in operation 606. In certain examples, operation 604 may also include hearing device 202 generating and sending a nonce to client 204. In such examples, client 204 may also send the generated nonce to authorization system 100 together with the device characteristic data in operation 604.

In response to the request sent from client 204, system 100 may utilize the device characteristic data in any suitable manner to determine whether the request is valid in operation 504. For example, similar to sequence diagram 500 shown in FIG. 5, system 100 may determine in operation 608 of sequence diagram 600 that the requested operation would result in hearing device 202 operating in an unsafe or improper manner. In such a situation, system 100 may abort the process such that hearing device 202 does not perform the operation. Alternatively, system 100 may determine that the request would result in hearing device 202 operating in a safe and acceptable manner. In response to such a determination, system 100 may transmit an authorization message to hearing device 202 in operation 610. In certain examples, the authorization message sent in operation 610 may be a signed authorization message that includes any suitable combination of information, such as described herein, to facilitate hearing device 202 successfully verifying the authorization message.

In response to the authorization message, hearing device 202 may verify the authorization message in operation 612. For example, hearing device 202 may analyze the authorization message in any suitable manner to verify whether the authorization message originated from system 100, was not manipulated, and is not corrupt. If hearing device 202 determines that the authorization message did not originate from system 100, was manipulated, and/or is corrupt, hearing device 202 may abort the process such that the operation requested by client 204 is not performed. On the other hand, if hearing device 202 determines that the authorization message originated from system 100, was not manipulated, and is not corrupt, hearing device 202 may perform the operation requested by client 204 in operation 614.

In the exemplary sequence diagram 700 shown in FIG. 7, a write-protected public key and write-protected device characteristic data are stored in a memory of hearing device 202 (e.g., in memory 402). In addition, a corresponding private key is stored in a memory of system 100 (e.g., memory 102). The public-private key pair is used in sequence diagram 700 to authenticate an authorization message. In operation 702, client 204 may send a request to system 100 for hearing device 202 to perform an operation. In operation 704, hearing device 202 may generate a nonce. In operation 706, hearing device 202 may send device characteristic data and the nonce to client 204. After client 204 receives the device characteristic data and the nonce, client 204 may send the device characteristic data and the nonce to system 100 in operation 708.

After system 100 receives the device characteristic data and the nonce, system 100 may input the device characteristic data into a hearing device fitting model in operation 710. Based on an output of the hearing device fitting model, system 100 may determine whether the request from client 204 is valid for hearing device 202. For example, similar to sequence diagram 500 shown in FIG. 5, system 100 may determine in operation 712 of sequence diagram 700 that the requested operation would result in hearing device 202 operating in an unsafe or improper manner. In such a situation, system 100 may abort the process such that hearing device 202 does not perform the operation. Alternatively, system 100 may determine that the request would result in hearing device 202 operating in a safe and acceptable manner. In response to such a determination, system 100 may send a signed authorization message to client 204 in operation 714. The signed authorization message may be generated by system 100 in any suitable manner using the private key to generate the message's signature.

In operation 716, client 204 may send the signed authorization message to hearing device 202. For example, client 204 may send the signed authorization message to hearing device 202 by way of network 206.

In response to the signed authorization message, hearing device 202 may verify the signed authorization message in operation 718. For example, hearing device 202 may use the public key to analyze the signed authorization message and verify whether the authorization message originated from system 100, was not manipulated, and is not corrupt. If hearing device 202 determines that the authorization message did not originate from system 100, was manipulated, and/or is corrupt, hearing device 202 may abort the process such that the operation requested by client 204 is not performed by hearing device 202. On the other hand, if hearing device 202 determines that the authorization message originated from system 100, was not manipulated, and is not corrupt, hearing device 202 may perform the operation requested by client 204 in operation 720.

Although FIG. 7 shows operations 702 and 708 as being separate operations, it is understood that the request, the device characteristic data, and the nonce may be sent to system 100 in the same communication in certain implementations. In addition, in certain implementations, hearing device 202 may be configured to send the device characteristic data and the nonce to system 100 without going through client 204. Similarly, in certain examples, system 100 may send the signed authorization message to hearing device 202 without going through client 204.

Moreover, in certain examples, hearing device 202 may generate the nonce and send the device characteristic data in response to a request provided from client 204 and/or system 100. For example, prior to client 204 sending the request to system 100 in operation 702, client 204 may send the request to hearing device 202. In response to the request, hearing device 202 may generate the nonce and send the device characteristic data system 100.

In certain examples, hearing device 202 may further send a confirmation message to client 204 and/or system 100 that confirms that the operation requested by client 204 has been performed.

In certain alternative examples, hearing device 202 may be pre-registered and authenticated with system 100 prior to system 100 determining whether a given operation is valid for hearing device 202. In such examples, system 100 may receive and store the device characteristic data associated with hearing device 202 when hearing device 202 is registered. When client 204 requests that an operation be performed by hearing device 202, hearing device 202 may either not have to transmit the device characteristic data to system 100 or may transmit either updated device characteristic data or only some of the device characteristic data to system 100.

In certain alternative examples, system 100 may be implemented by a computing device (e.g., a smartphone, laptop computer, tablet computer, etc.) operated by a recipient of hearing device 202. In such examples, system 100 may be implemented as an application operating on the computing device that allows the recipient to act as an administrator to control authorization of operations to be performed by hearing device 202. Through the application, system 100 may allow the recipient to control any suitable aspect associated with authorizing operations to be performed by hearing device 202. For example, system 100 may allow the recipient, through the application, to grant permissions to different clients to, for example, update firmware, change operating parameters, change settings, etc. associated with hearing device 202.

In some examples, a non-transitory computer-readable medium storing computer-readable instructions may be provided in accordance with the principles described herein. The instructions, when executed by a processor of a computing device, may direct the processor and/or computing device to perform one or more operations, including one or more of the operations described herein. Such instructions may be stored and/or transmitted using any of a variety of known computer-readable media.

A non-transitory computer-readable medium as referred to herein may include any non-transitory storage medium that participates in providing data (e.g., instructions) that may be read and/or executed by a computing device (e.g., by a processor of a computing device). For example, a non-transitory computer-readable medium may include, but is not limited to, any combination of non-volatile storage media and/or volatile storage media. Exemplary non-volatile storage media include, but are not limited to, read-only memory, flash memory, a solid-state drive, a magnetic storage device (e.g. a hard disk, a floppy disk, magnetic tape, etc.), ferroelectric random-access memory ("RAM"), and an optical disc (e.g., a compact disc, a digital video disc, a Blu-ray disc, etc.). Exemplary volatile storage media include, but are not limited to, RAM (e.g., dynamic RAM).

Figure 8:
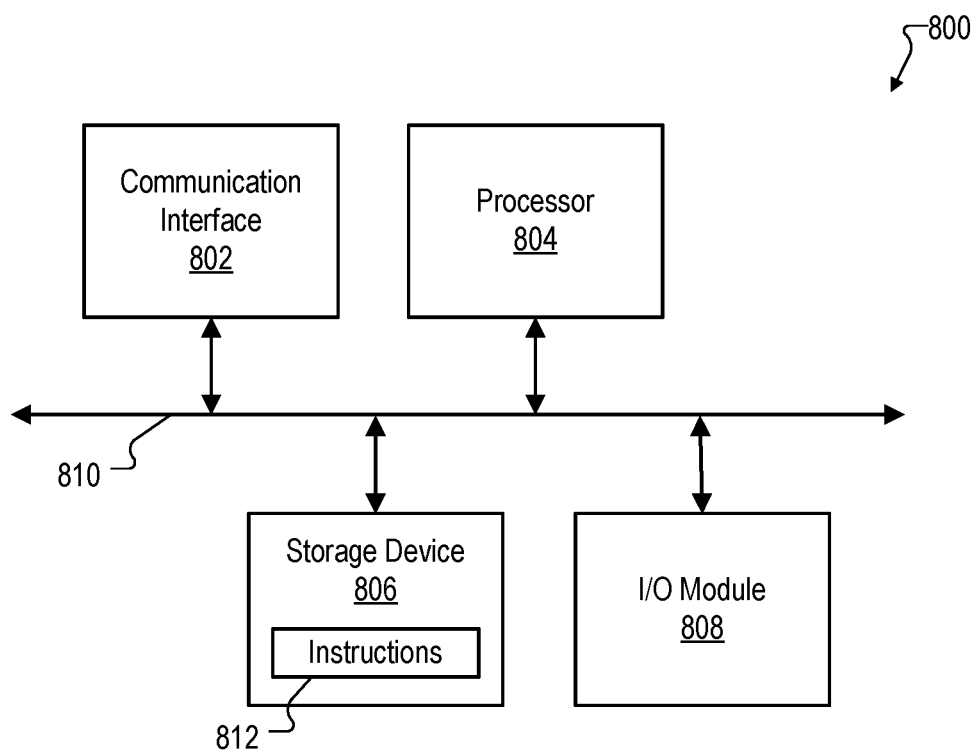
FIG. 8 illustrates an exemplary computing device according to principles described herein.

FIG. 8 illustrates an exemplary computing device 800 that may be specifically configured to perform one or more of the processes described herein. As shown in FIG. 8, computing device 800 may include a communication interface 802, a processor 804, a storage device 806, and an input/output ("I/O") module 808 communicatively connected one to another via a communication infrastructure 810. While an exemplary computing device 800 is shown in FIG. 8, the components illustrated in FIG. 8 are not intended to be limiting. Additional or alternative components may be used in other embodiments. Components of computing device 800 shown in FIG. 8 will now be described in additional detail.

Communication interface 802 may be configured to communicate with one or more computing devices. Examples of communication interface 802 include, without limitation, a wired network interface (such as a network interface card), a wireless network interface (such as a wireless network interface card), a modem, an audio/video connection, and any other suitable interface.

Processor 804 generally represents any type or form of processing unit capable of processing data and/or interpreting, executing, and/or directing execution of one or more of the instructions, processes, and/or operations described herein. Processor 804 may perform operations by executing computer-executable instructions 812 (e.g., an application, software, code, and/or other executable data instance) stored in storage device 806.

Storage device 806 may include one or more data storage media, devices, or configurations and may employ any type, form, and combination of data storage media and/or device. For example, storage device 806 may include, but is not limited to, any combination of the non-volatile media and/or volatile media described herein. Electronic data, including data described herein, may be temporarily and/or permanently stored in storage device 806. For example, data representative of computer-executable instructions 812 configured to direct processor 804 to perform any of the operations described herein may be stored within storage device 806. In some examples, data may be arranged in one or more databases residing within storage device 806.

I/O module 808 may include one or more I/O modules configured to receive user input and provide user output. One or more I/O modules may be used to receive input for a single virtual experience. I/O module 808 may include any hardware, firmware, software, or combination thereof supportive of input and output capabilities. For example, I/O module 808 may include hardware and/or software for capturing user input, including, but not limited to, a keyboard or keypad, a touchscreen component (e.g., touchscreen display), a receiver (e.g., an RF or infrared receiver), motion sensors, and/or one or more input buttons.

I/O module 808 may include one or more devices for presenting output to a user, including, but not limited to, a graphics engine, a display (e.g., a display screen), one or more output drivers (e.g., display drivers), one or more audio speakers, and one or more audio drivers. In certain embodiments, I/O module 808 is configured to provide graphical data to a display for presentation to a user. The graphical data may be representative of one or more graphical user interfaces and/or any other graphical content as may serve a particular implementation.

In some examples, any of the systems, hearing devices, and/or other components described herein may be implemented by computing device 800. For example, memory 102 or memory 402 may be implemented by storage device 806, and processor 104 or processor 404 may be implemented by processor 804.

To the extent the aforementioned embodiments collect, store, and/or employ personal information provided by individuals, it should be understood that such information may be used in accordance with all applicable laws concerning protection of personal information. Additionally, the collection, storage, and use of such information may be subject to consent of the individual to such activity, for example, through "opt-in" or "opt-out" processes as may be appropriate for the situation and type of information. Storage and use of personal information may be in an appropriately secure manner reflective of the type of information, for example, through various encryption and anonymization techniques for particularly sensitive information.

In the preceding description, various exemplary embodiments have been described with reference to the accompanying drawings. It will, however, be evident that various modifications and changes may be made thereto, and additional embodiments may be implemented, without departing from the scope of the invention as set forth in the claims that follow. For example, certain features of one embodiment described herein may be combined with or substituted for features of another embodiment described herein. The description and drawings are accordingly to be regarded in an illustrative rather than a restrictive sense.

What is claimed is:

1. An authorization system located remotely from a hearing device that is configured to facilitate hearing by a recipient, the authorization system comprising:
   a memory storing instructions; and
   a processor communicatively coupled to the memory and configured to execute the instructions to:
      receive, from a client anonymous to the authorization system and in communication with the hearing device, a request for the hearing device to perform an operation;

determine, based on device characteristic data that is representative of one or more characteristics specific to the hearing device, that the operation is valid for the hearing device; and transmit, in response to determining that the operation is valid for the hearing device, an authorization message to the hearing device, the authorization message authorizing the hearing device to perform the operation requested by the client.

2. The authorization system of claim 1, wherein the processor is further configured to execute the instructions to receive the device characteristic data from the hearing device.

3. The authorization system of claim 1, wherein the processor is further configured to execute the instructions to send, in response to the receiving of the request from the client, a request to the hearing device requesting that the hearing device transmit the device characteristic data to the authorization system.

4. The authorization system of claim 1, wherein at least some of the device characteristic data is write-protected in a memory of the hearing device.

5. The authorization system of claim 1, wherein
the operation requested by the client includes an instruction to modify a setting that is not modifiable by the hearing device or the client unless authorized by the authorization system.

6. The authorization system of claim 1, wherein:
the transmitting of the authorization message includes using asymmetric cryptography to authenticate the authorization message, the asymmetric cryptography including using a private key stored in the memory of the authorization system and a corresponding public key stored in a memory of the hearing device; and
the processor is further configured to execute the instructions to receive, from the hearing device, a nonce generated by the hearing device.

7. The authorization system of claim 6, wherein the authorization message includes a signed authorization message that includes a signature that is generated based on the private key stored in the memory of the authorization system and that includes the nonce generated by the hearing device.

8. The authorization system of claim 1, wherein the determining that the operation is valid for the hearing device includes:
inputting the device characteristic data into a hearing device fitting model; and
determining, based on the hearing device fitting model, that the operation will result in the hearing device operating properly.

9. The authorization system of claim 1, wherein the processor is further configured to execute the instructions to:
receive, from the client, an additional request for the hearing device to perform an additional operation;
determine, based on the device characteristic data, that the additional operation is not valid for the hearing device; and
prevent the hearing device from performing the operation.

10. A hearing device configured to facilitate hearing by a recipient, the hearing device comprising:
a memory storing instructions and device characteristic data that is representative of one or more characteristics specific to the hearing device; and
a processor communicatively coupled to the memory and configured to execute the instructions to:
provide the device characteristic data to an authorization system located remotely from the hearing device, the device characteristic data provided to facilitate the authorization system authorizing the hearing device to perform an operation requested by a client that is anonymous to the authorization system, that is in communication with the hearing device, and that is communicatively coupled by way of a network to the authorization system;
receive, from the authorization system, an authorization message based on the device characteristic data and authorizing the hearing device to perform the operation requested by the client; and
perform, based on the authorization message received from the authorization system, the operation requested by the client.

11. The hearing device of claim 10, wherein the providing of the device characteristic data includes transmitting the device characteristic data to the authorization system directly or through the client by way of the network.

12. The hearing device of claim 10, wherein the authorization message is received from the authorization system directly or through the client.

13. The hearing device of claim 10, wherein at least some of the device characteristic data stored in the memory of the hearing device is write-protected.

14. The hearing device of claim 10, wherein
the operation requested by the client includes a request to modify a setting of the hearing device that is not modifiable by the hearing device or the client unless authorized by the authorization system.

15. The hearing device of claim 10, wherein:
the authorization message is authenticated using asymmetric cryptography in which a public key is stored in the memory of the hearing device and a corresponding private key is stored in a memory of the authorization system;
the processor is further configured to execute the instructions to generate and send a nonce to the authorization system;
the authorization message is a signed authorization message that includes a signature that is generated based on the private key stored in the memory of the authorization system and that includes the nonce;
the processor is further configured to execute the instructions to use the public key and the nonce to verify the signature; and
the operation is only performed when the signature is successfully verified.

16. The hearing device of claim 10, wherein the processor is further configured to execute the instructions to transmit a confirmation message to the client indicating that the operation has been performed.

17. A system comprising:
a hearing device configured to facilitate hearing by a recipient and store device characteristic data representative of device characteristics specific to the hearing device;
a client in communication with the hearing device; and
an authorization system located remotely from the hearing device and the client, the client anonymous to the authorization system, the authorization system configured to:
receive, from the client, a request for the hearing device to perform an operation;
determine, based on the device characteristic data, that the operation is valid for the hearing device; and
transmit, in response to determining that the operation is valid for the hearing device, an authorization message to the hearing device, the authorization message authorizing the hearing device to perform the operation requested by the client.

18. The system of claim 17, wherein the operation includes a request to modify a setting that is not modifiable by the hearing device or the client unless authorized by the authorization system.

19. The system of claim 17, wherein the hearing device is anonymous to the authorization system.

20. The system of claim 17, wherein the authorization system is further configured to receive the device characteristic data from the hearing device based on the request for the hearing device to perform the operation.

* * * * *